(12) United States Patent
Smith

(10) Patent No.: US 9,427,535 B2
(45) Date of Patent: Aug. 30, 2016

(54) TRIGGER MECHANISM FOR A DRUG DELIVERY DEVICE

(75) Inventor: Christopher James Smith, Cheshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1087 days.

(21) Appl. No.: 13/202,824

(22) PCT Filed: Mar. 17, 2010

(86) PCT No.: PCT/EP2010/053433
§ 371 (c)(1),
(2), (4) Date: Dec. 21, 2011

(87) PCT Pub. No.: WO2010/106090
PCT Pub. Date: Sep. 23, 2010

(65) Prior Publication Data
US 2012/0103329 A1 May 3, 2012

(30) Foreign Application Priority Data

Mar. 17, 2009 (EP) .................................. 09003805

(51) Int. Cl.
*A61M 15/00* (2006.01)
*A61M 11/00* (2006.01)
*A61M 5/20* (2006.01)

(52) U.S. Cl.
CPC ........ *A61M 15/0091* (2013.01); *A61M 5/2033* (2013.01); *A61M 11/007* (2014.02); *A61M 15/009* (2013.01); *A61M 2005/2013* (2013.01); *A61M 2202/064* (2013.01); *A61M 2205/8281* (2013.01)

(58) Field of Classification Search
CPC ......... A61M 11/007–11/009; A61M 15/0091; A61M 15/95–15/98; A61M 5/20; A61M 2005/2026; A61M 2005/2053; A61M 2005/202; A61M 2205/8275; A61M 2205/8281; A61M 11/08
USPC ............ 128/200.14, 200.22, 200.23, 200.24, 128/200.21, 203.15, 203.21, 203.26, 128/205.23, 205.24
See application file for complete search history.

(56) References Cited

U.S. PATENT DOCUMENTS

| | | | |
|---|---|---|---|
| 5,349,945 A * | 9/1994 | Wass et al. | 128/200.23 |
| 6,405,727 B1 | 6/2002 | MacMichael et al. | |
| 7,270,124 B2 * | 9/2007 | Rasmussen | 128/200.23 |
| 7,721,731 B2 * | 5/2010 | Bacon | 128/200.23 |
| 2004/0020486 A1 | 2/2004 | Huxham et al. | |
| 2004/0107962 A1 * | 6/2004 | Harrison et al. | 128/200.23 |
| 2007/0118094 A1 | 5/2007 | Bingham et al. | |
| 2010/0307493 A1 * | 12/2010 | Kirniak | 128/203.15 |

* cited by examiner

OTHER PUBLICATIONS

Form PCT/IB/326, Notification Concerning Transmittal of International Preliminary Report on Patentability.

*Primary Examiner* — Bradley Philips
(74) *Attorney, Agent, or Firm* — McDonnell Boehnen Hulbert & Berghoff LLP

(57) ABSTRACT

The invention relates to a trigger mechanism for a drug delivery device comprising at least one energy storing element, an actuation element and a series of cascaded trigger elements. The trigger elements are pre-stressed with increasing pre-stressing and coupled to the at least one energy storing element such that the trigger elements, upon exerting a sufficient actuation force (Fa, U) on the actuation element, cause a cascaded release of increasing portions of energy stored in the at least one energy storing device. At least one of the trigger elements is equipped with a latch element directly coupling at least two trigger elements such that the latch element restrains at least one of these trigger elements to its pre-stressed state before exerting the actuation force (Fa, U).

10 Claims, 2 Drawing Sheets

TRIGGER MECHANISM FOR A DRUG DELIVERY DEVICE

CROSS REFERENCE TO RELATED APPLICATIONS

The present application is a 35 U.S.C. 371 National Application of PCT/EP2010/053433 filed Mar. 17, 2010, which claims priority to European Patent Application No. 09003805.0, filed Mar. 17, 2009, the entire contents of which are incorporated entirely herein by reference.

FIELD OF THE INVENTION

The invention relates to a trigger mechanism for a drug delivery device comprising at least one energy-storing element and to a drug delivery device with such a trigger mechanism.

BACKGROUND OF THE INVENTION

Drug delivery devices, such as inhalers or injection devices, that can be easily operated by a patient himself are well known in the art. Generally, such devices have trigger mechanisms to actuate drug dispensing.

For instance, there are trigger mechanisms designed as breath-actuation mechanisms in mechanically powered inhalers, such as a dry powder inhaler (DPI), an aqueous droplet inhaler (ADI) and/or a metered dose inhaler (MDI).

US 2004 020486 A1 discloses an inhaler for delivery of medicament from a canister which is compressible to deliver a dose of medicament. The inhaler comprises a housing for holding a canister. The housing having a mouthpiece for inhalation of a dose of medicament delivered by the canister. Furthermore the inhaler includes a breath-actuated actuation mechanism for compressing a canister held in the housing in response to inhalation at the mouthpiece. The actuation mechanism includes a locking mechanism arranged to lock the canister in a compressed state. The locking mechanism has a vane in the form of a flap and being responsive to the inhalation at the mouthpiece to release the canister when the level of inhalation at the mouthpiece falls below a predetermined threshold. It is necessary for the user to take e deep breath to ensure proper inhalation of the medicament so the delay for reset of the canister is sufficient long.

U.S. Pat. No. 6,405,727 B1 discloses a dosing device comprising a dispensing means for dispensing a dose material, a first biasing means for engaging with the dispensing means, and a dose activating mechanism. The dose activating mechanism comprises a deflectable member moveable by airflow, and a series of at least two moveable elements which transmit movement of the first element in the series to the last element in the series by a cascade effect, such that movement of the deflectable member is transferred to the first element of the series and a second biasing means communicates with one the at least two moveable elements. As movement is transferred between the moveable elements, energy stored in the second biasing means is released to increase the force associated with the movement of the moveable elements.

US 2007 118094 A1 discloses a needle-less injector device for delivering a dose of fluid intradermally, subcutaneously or intramuscularly to an animal or human. The device includes an inner housing having opposed ends. A syringe is disposed in one end of the inner housing. The syringe includes a nozzle for delivering a dose of fluid held within the syringe. A plunger is movably disposed within the syringe. A spring-powered hammer is movably disposed within the inner housing. The hammer cooperates with the plunger to drive the dose of medicament from the nozzle. An injection delivery spring for powering the hammer is positioned and compressed between the other vend of the inner housing and the spring powered hammer. An outer housing slideably supports the inner housing. A skin tensioning spring is mounted between the inner housing and the outer housing, the skin tensioning spring biasing the nozzle of the syringe against the animal or human. A trigger mechanism is disposed in the outer housing, the trigger mechanism cooperating with the spring powered hammer to release the injection delivery spring, wherein the size of the injection delivery spring and the length of the hammer dictate the amount of dose delivered and whether the dose is delivered intradermally, subcutaneously or intramuscularly to an animal or human.

SUMMARY OF THE INVENTION

It is an object of the present invention to provide an improved trigger mechanism for a drug delivery device, in particular to actuate drug dispensing, and an improved drug delivery device.

The object is achieved by a trigger mechanism according to claim 1 and by a drug delivery device according to claim 9.

Preferred embodiments of the invention are given in the dependent claims.

According to the present invention there is provided a trigger mechanism for a drug delivery device comprising at least one energy storing element, an actuation element and a series of cascaded trigger elements. The trigger elements are pre-stressed with increasing pre-stressing and coupled to the at least one energy storing element such that the trigger elements, upon exerting a sufficient actuation force on the actuation element, cause a cascaded release of increasing portions of energy stored in the at least one energy storing device. Thereby at least one of the trigger elements is equipped with a latch element directly coupling at least two trigger elements such that the latch element restrains at least one of these trigger elements to its pre-stressed state before exerting the actuation force.

The cascaded release of increasing portions of stored energy has the advantage that a large amount of energy can be released through a relatively small actuation force. This is particularly useful for drug delivery devices that are to be actuated by very small amount of trigger energy, for example for an inhaler that is to be actuated by a flap that is moved by a flow of inhaled air or a device to be actuated by a button pressed by a finger or an autoinjector that is actuated by pressing against a patients body.

The cascaded release of increasing portions of stored energy by a cascaded series of trigger elements thereby advantageously solves the problem that stored energy usually creates resistance to the movement of a trigger, typically in the form of friction. This resistance therefore limits the amount of stored energy that a trigger can release. Using a cascade of trigger elements, one trigger element in the series can trigger a subsequent trigger element in the series using a portion of stored energy, thereby increasing successively the portion of stored energy that can be released by trigger elements.

Equipping trigger elements with latch elements directly coupling trigger elements in the series simplifies the cascaded trigger mechanism as compared to indirect couplings, e.g. through intermediate coupling elements, and reduces both the manufacturing expense and the size of the trigger mechanism. Furthermore it can reduce the probability of a malfunction of the trigger mechanism due to the reduction of the number of components, which is particularly desirable when the trigger mechanism is used in drug delivery devices for life-saving drugs. In addition it can simplify the procedure to reset the trigger mechanism after drug delivery, again due to the reduction of the number of components and to the simplification of the couplings between the trigger elements.

In a preferred embodiment at least one of the trigger elements is a pivoted lever.

Pivoted levers are particularly suited as trigger elements as the can be easily coupled to one another and are cheap and simple components.

When using pivoted levers as trigger elements, preferably at least one latch element is a protrusion, in particular designed as a ring segment, and located at a pivot of a pivoted lever.

A protrusion located at a pivot of a pivoted lever is particularly suited to a cascaded coupling of trigger elements as it can restrain another trigger element from moving, and decouple this trigger element from the lever as the lever rotates, thereby supporting the cascade effect in a simple and effective manner.

Furthermore, in preferred embodiment the pivots of all pivoted levers are preferably located in the same plane.

This enables a particularly simple and effective construction of the trigger mechanism by a chain of pivoted levers.

In another preferred embodiment, at least one latch element is a notch in the surface of a trigger element.

A notch in the surface of a trigger element is another suitable means to couple two trigger elements in a simple and effective manner by engaging one trigger element in the notch of a neighbouring trigger element and disengaging it within the cascade effect.

Preferably at least one energy-storing element is a spring.

Springs are particularly suited as energy storing elements for the trigger mechanism for they are simple and cheap components that can store energy effectively and that can be easily reset and connected to trigger elements.

Furthermore, preferably the trigger elements correspond one-to-one to energy storing elements and each trigger element is coupled to the corresponding energy storing element.

In this way each trigger element is coupled precisely to one energy-storing element. This makes it particularly easy to realize a cascaded release of increasing portions of stored energy as each trigger element in the series can control its "own" energy storing element and trigger the release of energy stored in it during the cascade effect.

Preferably the actuation element is equipped with a latch element directly coupling it to one of the trigger elements.

In this way the actuation of the cascade effect can be easily realized by making the actuation element effectively part of the series of trigger elements.

Furthermore, in a preferred embodiment the cascaded release of increasing portions of stored energy amplifies an actuation force exerted on the actuation element to a force exertable through one of the trigger elements.

An amplification of the actuation force is particularly advantageous in drug delivery devices which the force required for drug delivery exceeds the actuation force exertable on the actuation element.

According to the present invention, there is further provided a drug delivery device equipped with a trigger mechanism according to any one of these embodiments, in which the trigger mechanism is a release mechanism to actuate and release delivery of a dose of a drug stored in the drug delivery device.

A preferred embodiment of such a drug delivery device is an inhaler, in particular an inhaler whose actuation element is a pivoted actuation flap movable by gas or fluid flow.

Another preferred embodiment of such a drug delivery device is an autoinjector.

The trigger mechanism is particularly suited as a release mechanism for drug delivery through inhalers and autoinjectors as these devices are typically actuated by an actuation force that is smaller than the force required for drug delivery.

In a preferred embodiment of a drug delivery device at least one of the trigger elements is a piston by means of which a pressure is exertable to the drug.

The use of a piston as a trigger element is particularly advantageous when the drug to be delivered by the drug delivery device is a fluid or a gas because such drugs may be best delivered by a pressure exerted to the drug.

BRIEF DESCRIPTION OF THE DRAWINGS

These and other objects, features, aspects, and advantages of the present invention will become more apparent from the following detailed description of preferred embodiments and accompanying drawings, in which.

DETAILED DESCRIPTION OF PREFERRED EMBODIMENTS

Figure 1A:
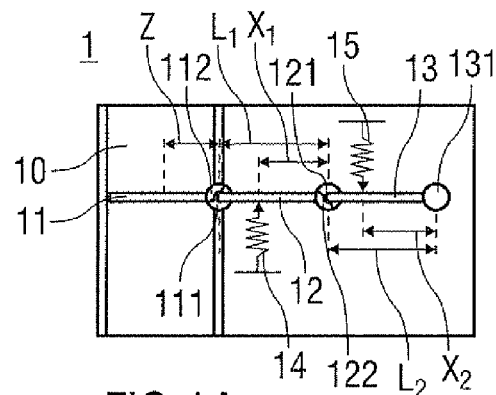
FIGS. 1A through 1D illustrate schematically a first embodiment of a trigger mechanism for an inhaler to actuate delivery of a dose of a drug.

FIGS. 1A through 1D illustrate a first embodiment of a trigger mechanism according to the invention. The trigger mechanism is used in an inhaler 1 to actuate delivery of a dose of a drug stored in the inhaler 1, for example a dry powder, aqueous droplet or metered dose inhaler. Successive stages of an actuation process for drug delivery are shown to explain the operation of the trigger mechanism.

The trigger mechanism comprises an actuation flap 11, a first lever 12, a second lever 13, a first spring 14 and a second spring 15.

The actuation flap 11 is located in a breathing channel 10 through which a user inhales. The actuation flap 11 and the levers 12, 13 are pivoted around pivots 111, 121, 131 at one of their ends respectively. The actuation flap 11 is equipped with a first ring segment 112 located at its pivot. The first lever 12 is equipped with a second ring segment 122 located at its pivot. The ring segments 112, 122 extend about one third of a circle around the centre of the respective pivot 111, 121 and extend from the surface of the respective pivot 111, 121.

The pivots 111 and 121 of the actuation flap 11 and of the first lever 12 are separated by a distance $L_1$ corresponding to a length of the first lever 12. The pivots 121 and 131 of the levers 12, 13 are separated by a distance $L_2$ corresponding to a length of the second lever 13. The pivots 111, 121, 131 are located in a common plane. Hence, when the actuation flap 11 and the levers 12, 13 are rotated to this plane and likewise oriented from their respective pivots 111, 121, 131 as shown in FIG. 1A, the first lever 12 extends to the pivot 111 of the actuation flap 11, and the second lever 13 extends to the pivot 121 of the first lever 12. Furthermore, in this position the first ring segment 112 restrains the first lever 12 from rotating upwards while the second ring segment 122 restrains the second lever 13 from rotating downwards.

The first lever 12 is coupled to the first spring 14 near to the pivot 111 of the actuation flap 11 at a distance $X_1$ to the pivot 121 of the first lever 12. The second lever 13 is coupled to the second spring 15 near to the pivot 121 of the first lever 12 at a distance $X_2$ to the pivot 131 of the second lever 13. Thereby the first spring 14 is located below the first lever 12 while the second spring 15 is located above the second lever 13. The stiffness of the second spring 15 exceeds the stiffness of the first spring 14.

FIG. 1A shows an initial state of the trigger mechanism with the actuation flap 11 and the levers 12, 13 located in the same plane as described above. In this state both springs 14, 15 are compressed, the second spring 15 storing more energy than the first spring 14. When no force is acting on the actuation flap 11, a rotation of the actuation flap 11 and the levers 12, 13 are restrained by the ring segments 112, 122 respectively. The levers 12, 13 are thus pre-stressed by the springs 14, 15 respectively, the pre-stressing of the second lever 13 exceeding the pre-stressing of the first lever 12.

Figure 1B:
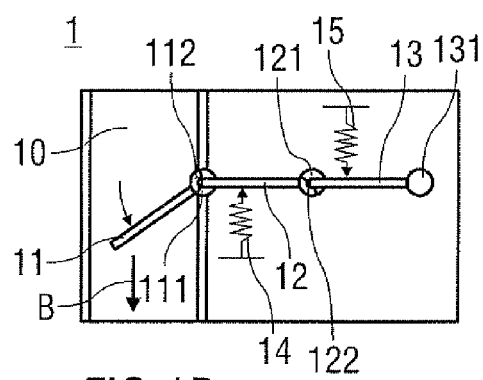

FIG. 1B shows the trigger mechanism when a user just has started to inhale. The inhaling causes an airflow B and a pressure drop P which suffices to rotate the actuation flap 11 downwards. A detailed quantitative discussion of this mechanism is given below.

Figure 1C:
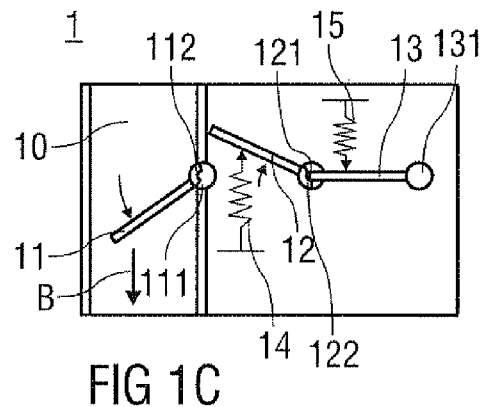

FIG. 1C shows the trigger mechanism when the actuation flap 11 has been rotated sufficiently so that the first ring segment 112 releases the first lever 12. As a consequence, the first spring 14 expands and rotates the first lever 12 upwards. This mechanism is also discussed in detail below.

Figure 1D:
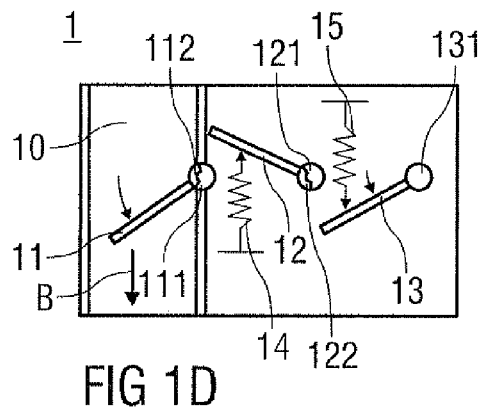

FIG. 1D shows the trigger mechanism when the first lever 12 has been rotated sufficiently so that the second ring segment 122 releases the second lever 13. As a consequence, the second spring 15 expands and rotates the second lever 13 downwards.

During the actuation process illustrated by the FIGS. 1A through 1D an actuation force Fa exerted by the pressure drop P on the actuation flap 11 releases energy stored in the first spring 14 which in turn is used to release energy stored in the second spring 15. Thereby the actuation force Fa can be considerably amplified to forces exerted by the springs 14, 15. This will be shown in the following quantitative analysis of the trigger mechanism described qualitatively above.

With A denoting the area of the actuation flap 11, the actuation force Fa exerted by the pressure drop P on the actuation flap 11 is $Fa=P \cdot A$. The actuation force Fa exerts an actuation torque $Ta = P \cdot A \cdot Z$ on the actuation flap 11 where Z is the distance between the pivot 111 of the actuation flap 11 and the effective application point of the actuation force Fa.

Denoting the spring force exerted by the first spring 14 on the first lever 12 by F1, a reaction force Y1 at the pivot 111 is $Y1=(X_1/L_1) \cdot F1$. In the initial state of the trigger mechanism shown in FIG. 1A, the rotation of the actuation flap 11 is restrained by a static friction between the first ring segment 112 and the corresponding end of the first lever 12. This static friction is mue $Y1=\mu \cdot (X_1/L_1) \cdot F1$ with $\mu$ a friction coefficient. Denoting the radius of the first ring segment 112 from the centre of the pivot 111 by $R_1$, the rotation of the actuation flap 11 is thus restrained by a first restraining torque $T1=R_1 \cdot \mu \cdot (X_1/L_1) \cdot F1$.

In order for the trigger mechanism to operate according to FIG. 1B, i.e. in order to rotate the actuation flap 11, this first restraining torque T1 must be exceeded by the actuation torque Ta, i.e. $T1<Ta$ and thus $R_1 \cdot \mu \cdot (X_1/L_1) \cdot F1 < Z \cdot P \cdot A$. Therefore, the force F1 of the first spring 12 that can be restrained by the trigger mechanism, and still released by actuation flap 11 is restricted by $$F1 < Z \cdot P \cdot A \cdot (L_1/X_1)/(R_1 \cdot \mu). \qquad [1]$$

and the maximal amplification of the actuation force Fa provided by the first spring 14 is restricted by $$F1/Fa < Z \cdot (L_1/X_1)/(R_1 \cdot \mu). \qquad [2]$$

Inserting typical values A=100 mm², Z=5 mm, P=1 kPa, $L_1$=40 mm, $X_1$=20 mm, $R_1$=1 mm and $\mu$=0.5, this results in $$F1 < 2 \text{ N} \qquad [3]$$

and $$F1/Fa < 20. \qquad [4]$$

An analogous consideration applies to the coupling of the first lever 12 to the second lever 13 through the second ring segment 122.

Denoting the spring force on the second lever 13 due to the second spring 15 by F2, a reaction force Y2 at the pivot 121 is $Y2=(X_2/L_2) \cdot F2$. The rotation of the first lever 12 is restrained by a static friction between the second ring segment 122 and the corresponding end of the second lever 13. This static friction is $\mu \cdot Y2 = \mu \cdot (X_2/L_2) \cdot F2$. Denoting the radius of the second ring segment 122 from the centre of the pivot 121 by $R_2$, the rotation of the first lever 12 is restrained by a second restraining torque $T2 = R_2 \cdot \mu \cdot (X_2/L_2) \cdot F2$.

In order for the trigger mechanism to operate according to FIG. 1C, i.e. in order to rotate the first lever 12, the second restraining torque T2 must be exceeded by the torque $X_1 \cdot F1$ provided by the first spring 14 on the first lever 12, i.e. $R_2 \cdot \mu \cdot (X_2/L_2) \cdot F2 < X_1 \cdot F1$.

Therefore, the additional force amplification F2/F1 is restricted by $$F2/F1 < X1 \cdot (L_2/X_2)/(R_2 \cdot \mu). \qquad [5]$$

Inserting the same typical values as above with $X_1=X_2=20$ mm, $L_1=L_2=40$ mm, $R_1=R_2=1$ mm, $\mu=0.5$, this yields $$F2/F1 < 80 \qquad [6]$$

and $$F2 < 160 \text{ N}. \qquad [7]$$

F2 could thus be up to about 160 N. This is a significant force and the energy released from the springs 14, 15 can indeed be used dose delivery through the inhaler 1. Additional cascaded trigger elements and springs could be added to enhance the force amplification even further.

A further use for the trigger mechanism could be that each lever 12, 13 could be connected to a separate part of the inhaler mechanism. For example, the first lever 12 could trigger opening of a dose container, the second lever 13 could trigger dose delivery. By adding damping to either the first lever 12 or the second lever 13 it would also be possible to introduce a time delay between the initial breath actuation of the actuation flap 11 and the release of the second lever 13. This could be used to introduce a "staged" response to the breath actuation.

After the levers 12, 13 have been released the user would have to reset both levers 12, 13 before the trigger mechanism could be used again. The reset action could occur simultaneously when the user performs some other action with the inhaler 1, for example opening it to remove an empty dose container or load a new dose container, or in a priming action of the inhaler 1 prior to use. The limit of how far a force could be amplified by the trigger mechanism is likely to be how much energy the user can put back into the system when resetting the trigger mechanism.

The embodiment shown in FIGS. 1A through 1D has the disadvantage that the springs 14, 15 have to be reset in opposite directions. This disadvantage is overcome by an alternative embodiment of the trigger mechanism shown in FIGS. 2A and 2B. Again, the trigger mechanism is used in an inhaler 1.

Figure 2A:
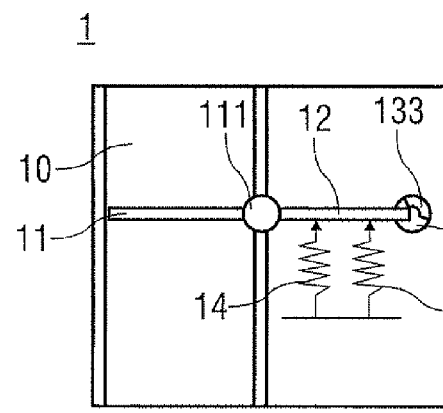
FIGS. 2A and 2B illustrate schematically a second embodiment of a trigger mechanism for an inhaler to actuate delivery of a dose of a drug.

A difference of this embodiment as compared to the first embodiment is that the levers 12, 13 are arranged such that they are stacked one above the other in an initial state of the trigger mechanism shown in FIG. 2A. Furthermore, the first lever 12 is fixed to the actuation flap 11, both having the same pivot 111 so that they can only rotate simultaneously. The springs 14, 15 are located on the same side of the levers 12, 13, and the second lever 13 is equipped with a third ring segment 133 of the same type as the ring segments 112, 122 of the first embodiment. The first lever 12 now extends from its pivot 111 to the pivot 131 of the second lever 13. Again, the pivot 111 is equipped with a first ring segment 112 (not visible in the FIGS. 2A and 2B) to which the second lever 13 extends in its initial position.

In the initial state of the trigger mechanism shown in FIG. 2A, the third ring segment 133 restrains the actuation flap 11 and the first lever 12 from rotating through the friction between the third ring segment 133 and the corresponding end of the first lever 12 and the first ring segment 112 restrains the second lever 13 from rotating through the friction between the first ring segment 112 and the corresponding end of the second lever 13.

Figure 2B:
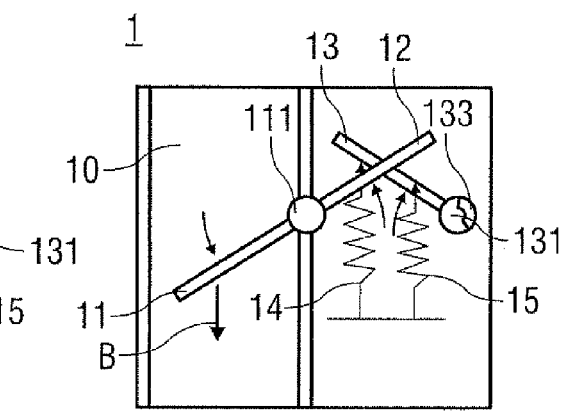

When a user exerts a sufficient actuation force Fa on the actuation flap 11 through inhaling, the levers 12 13 are released and both rotate upwards as shown in FIG. 2B.

In order to reset the trigger mechanism both levers 12, 13 are pushed downwards to reengage the ring segments 112, 133.

FIGS. 3A through 3D illustrate a third embodiment of a trigger mechanism according to the invention. The trigger mechanism is used in an autoinjector 2 to actuate delivery of a dose of a drug 242 stored in a cartridge 24 through a dispensing element 243 of the autoinjector 2 located at the bottom of the cartridge 24. The cartridge 24 is sealed by plug 241.

The trigger mechanism comprises a manually operated actuation lever 21, an intermediate lever 22, a piston 23, a first spring 26 and a second spring 25.

The actuation lever 21 is pivoted around a pivot 211 at one of its ends and is equipped with a trigger button at its opposite end. The distance between the centres of the pivot 211 and of the trigger button is denoted by $X_5$. The actuation lever 21 is equipped with a first ring segment 212 which is located at the pivot 211 and is of the same type as the ring segments 112, 122, 133 of the first and second embodiment.

The intermediate lever 22 is hook-shaped with a bend located at the pivot 211 of the actuation lever 21. A first end of the intermediate lever 22 is directed towards the piston 23, the second end contains a pivot around which the intermediate lever 22 is pivoted. The intermediate lever 22 is connected to the first spring 26 at a distance $X_3$ from its pivot. The distance between the bend and the pivot of the intermediate lever 22 is denoted by $X_4$.

One end of piston 23 is directed towards the plug 241 of the cartridge 24, the other end is connected to the second spring 25. The surface of the piston 23 is equipped with a notch in which the first end of the intermediate lever 22 can engage.

The operation of the trigger mechanism is now described first qualitatively with reference to FIGS. 3A through 3D and afterwards analysed quantitatively.

Figure 3A:
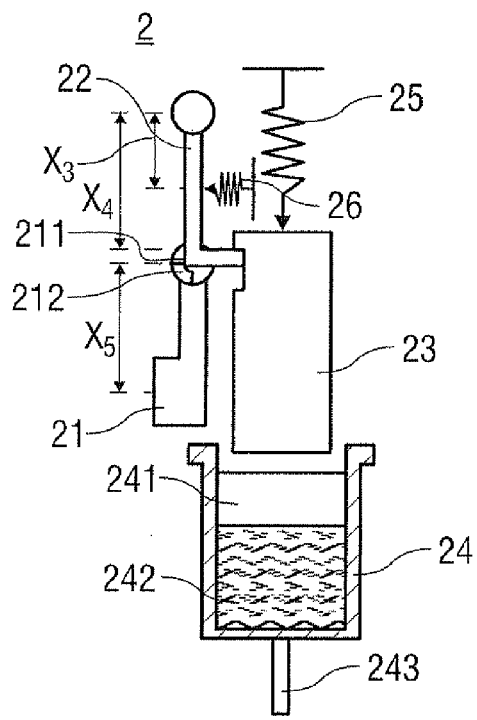
FIGS. 3A through 3D illustrate schematically a third embodiment of a trigger mechanism for an autoinjector to actuate delivery of a dose of a drug.

FIG. 3A shows an initial state of the trigger mechanism. Both springs 25, 26 are compressed. The first end of the intermediate lever 22 engages in the notch of the piston 23 and prevents the piston 23 from moving towards the plug 241. The bend of the intermediate lever 22 is coupled to the first ring segment 212 which restrains the intermediate lever 22 from rotating.

Figure 3B:
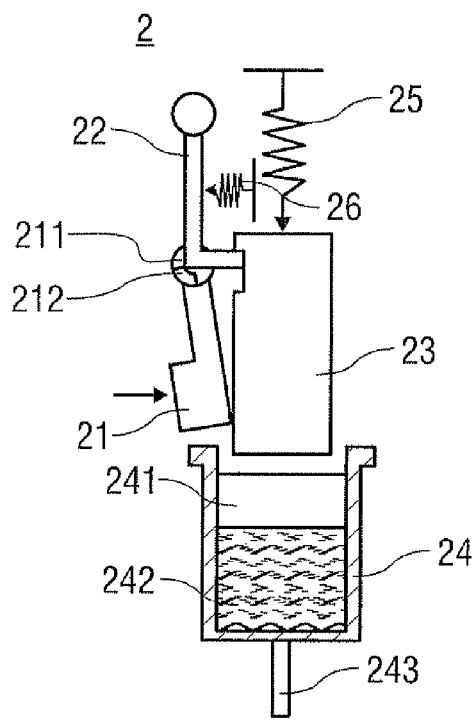

FIG. 3B shows the trigger mechanism when a user presses the trigger button of the actuation lever 21 sufficiently so that the actuation lever 21 is rotates around its pivot 211. As the actuation lever 21 rotates, the first ring segment 212 eventually disengages and releases the intermediate lever 22.

Figure 3C:
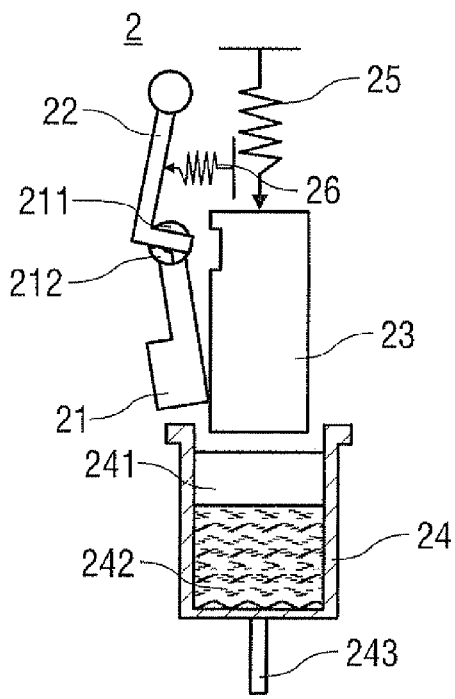

FIG. 3C shows the trigger mechanism after the intermediate lever 22 has been released. The first spring 26 expands and rotates the intermediate lever 22. The first end of the intermediate lever 22 disengages from the notch in the surface of the piston 23 which releases the piston 23. The piston 23 is now free to move towards the plug 241 under the action of the fourth spring 25.

Figure 3D:
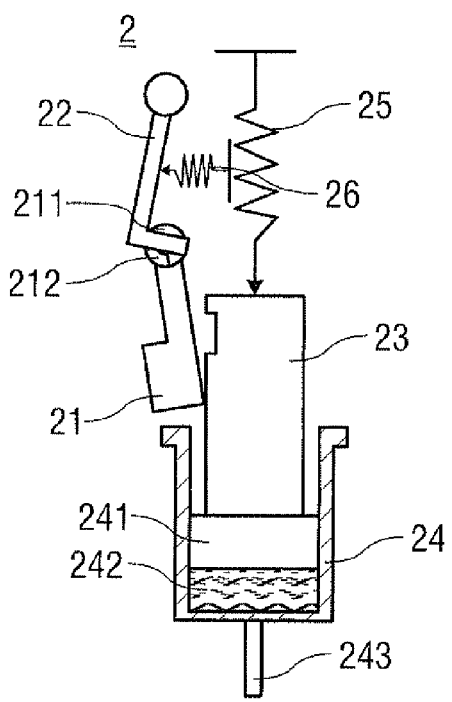

FIG. 3D shows the trigger mechanism after the piston 23 has been released. The piston 23 has moved to the plug 241 and pressed it towards the bottom of the cartridge 24. Thereby it exerts a pressure on the drug inside the cartridge 24 which forces delivery of the drug through the dispensing element 243.

To discuss the trigger mechanism quantitatively the spring forces of the third spring 26 and of the fourth spring 25 exerted on the intermediate lever 22 and the piston 23 in the initial state of the trigger mechanism are denoted by F3 and F4 respectively.

Assuming that the thickness of the intermediate lever 22 thickness is negligible compared to its length, the approximate reaction force provided by the first spring 26 between the intermediate lever 22 and the second ring segment 212 in the initial state of the trigger mechanism is $F3 \cdot (X_3/X_4)$. A third restraining torque T3 caused by friction between the intermediate lever 22 and the fourth ring segment 212 is therefore approximately $T3 = R_3 \cdot \mu \cdot F3 \cdot (X_3/X_4)$ where $R_3$ is the radius of the first ring segment 212 from the centre of the pivot 211.

A user must provide a sufficient actuation force U to the trigger button to overcome this resistance. The actuation torque resulting from U is $U \cdot X_5$.

The actuation lever 21 starts to rotate when this torque exceeds the third retraining torque T3, i.e. when $U \cdot X_5 > R_3 \cdot \mu \cdot F3 \cdot (X_3/X_4)$. Hence, for the actuation lever 21 to rotate, the force F3 of the third spring 26 is restricted by $$F3 < (X_4 \cdot X_5 / X_3) \cdot U / (R_3 \cdot \mu). \qquad [8]$$

In order to release the piston 23 the force $F3 \cdot (X_3/X_4)$ provided by the first spring 26 at the bend of the intermediate lever 22 must overcome the friction between the piston 23 and the intermediate lever 22 which is $\mu$ F4. Therefore, the piston 23 is released if $F3 \cdot (X_3/X_4) > \mu \cdot F4$. Hence, for the trigger mechanism to operate, the force F4 of the second spring 25 is restricted by $$F4 < F3 \cdot (X_3/X_4) / \mu. \qquad [9]$$

Inserting typical values $X_5=25$ mm, $X_3=15$ mm, $X_4=30$ mm, $\mu=0.5$, $R_3=2.5$ mm and $U=1$ N, one obtains $$F4<40 \text{ N}. \qquad [10]$$

As compared to the actuation force U=1 N this gives a force amplification up to a factor of 40. The amplification can be further enhanced by different arrangements of the intermediate lever 22 and/or the use of further intermediate levers and springs and/or a "rolling" coupling of the intermediate lever 22 to the piston 23 in place of the coupling through the notch in the surface of the piston 23.

LIST OF REFERENCES

1 inhaler
10 breathing channel
11 actuation flap
12,13,22 lever
14,15,25,26 spring
111,121,131,211 pivot
112,122,133,212 ring segment
2 autoinjector
21 actuation lever
22 intermediate lever
23 piston
24 cartridge
241 plug
242 drug
243 dispensing element
$X_1, X_2, X_3, X_4, X_5, L_1, L_2, Z$ distance
B air flow
P pressure drop
Fa, U actuation force
F1,F2,F3,F4 spring force
Y1,Y2 reaction force
Ta actuation torque
T1,T2,T3 restraining torque
$R_1, R_2, R_3$ radius
$\mu$ friction coefficient

The invention claimed is:

1. Drug delivery device equipped with a trigger mechanism, wherein the drug delivery device is an inhaler, the trigger mechanism comprising
   a first spring and a second spring,
   an actuation element, and
   a series of cascaded trigger elements pre-stressed with increasing pre-stressing, wherein the series of cascaded trigger elements are coupled to the first spring and the second spring,
   wherein upon exerting a sufficient actuation force (Fa, U) on the actuation element the trigger elements cause a cascaded release of increasing portions of energy stored in the first spring and the second spring,
   characterized in that a first trigger element is equipped with a latch element directly and releasably coupling at least two trigger elements, wherein the latch element directly couples the first trigger element to a second trigger element to restrain the second trigger element to its pre-stressed state before the actuation force (Fa, U) is exerted.

2. Drug delivery device according to claim 1, characterized in that at least one of the trigger elements is a pivoted lever.

3. Drug delivery device according to claim 2, characterized in that at least one latch element is a protrusion located at a pivot of a pivoted lever.

4. Drug delivery device according to claim 3, characterized in that the protrusion is designed as a ring segment.

5. Drug delivery device according to claim 2, characterized in that pivots of all pivoted levers are located in a same plane.

6. Drug delivery device according to claim 1, characterized in that the trigger elements are a first lever and a second lever and correspond one-to-one to the first spring and the second spring, and the first lever is coupled to the first spring and the second lever is coupled to the second spring.

7. Drug delivery device according to claim 1, characterized in that the actuation element is equipped with a latch element directly coupling it to one of the trigger elements.

8. Drug delivery device according to claim 1, characterized in that the cascaded release of increasing portions of stored energy amplifies the actuation force (Fa, U) to a force exertable through one of the trigger elements.

9. Drug delivery device according to claim 1, characterized in that the trigger mechanism is a release mechanism to actuate and release delivery of a dose of a drug stored in the drug delivery device.

10. Drug delivery device according to claim 1, characterized in that the actuation element is a pivoted actuation flap movable by gas or fluid flow.

* * * * *